United States Patent [19]

Winnek

[11] 3,984,684
[45] Oct. 5, 1976

[54] THREE-DIMENSIONAL RADIOGRAPHY
[76] Inventor: Douglas Fredwill Winnek, 10450 W. Loyola Drive, Los Altos Hills, Calif. 94022
[22] Filed: Feb. 6, 1974
[21] Appl. No.: 407,707

[52] U.S. Cl. .............................. 250/313; 250/320; 250/323; 250/445 T
[51] Int. Cl.² ................................... G03C 9/08
[58] Field of Search .......................... 250/320–323, 250/445 T, 468, 469, 313, 508, 509

[56] References Cited
UNITED STATES PATENTS
3,783,282   1/1974   Hoppenstein ................. 250/509 X

*Primary Examiner*—Paul L. Gensler

[57] ABSTRACT

Apparatus and a method for making an X-ray photograph of an object wherein the photograph, when viewed through a lenticular screen or other similar device, will provide a three-dimensional picture of the object and the interior parts thereof. The method is carried out by successively directing the X-ray beams from a conventional X-ray tube through the object, then through a parallax grating, and finally onto the film. The grating is mounted on the film support member and the object and film support member together are translated in parallel paths laterally with respect to the beam path at different speeds sufficient to maintain the film and object in congruent alignment with the X-ray tube. Since the position of the grating is fixed relative to the film, the grating moves slightly out of congruency causing the beam passing through the grating to slightly scan the film during the traverse. During traverse, the angle at which the object is exposed to radiation from the X-ray tube gradually changes. The resulting image on the film is a series of side-by-side variable aspect views or images of the object, corresponding in number to the number of slits in the grating, which can be viewed in three-dimension with the lenticular screen. Accurate measurements of the depth, size and motion of one or more internal parts of the object can be determined from measurements of those parts when viewed through the lenticular screen.

16 Claims, 11 Drawing Figures

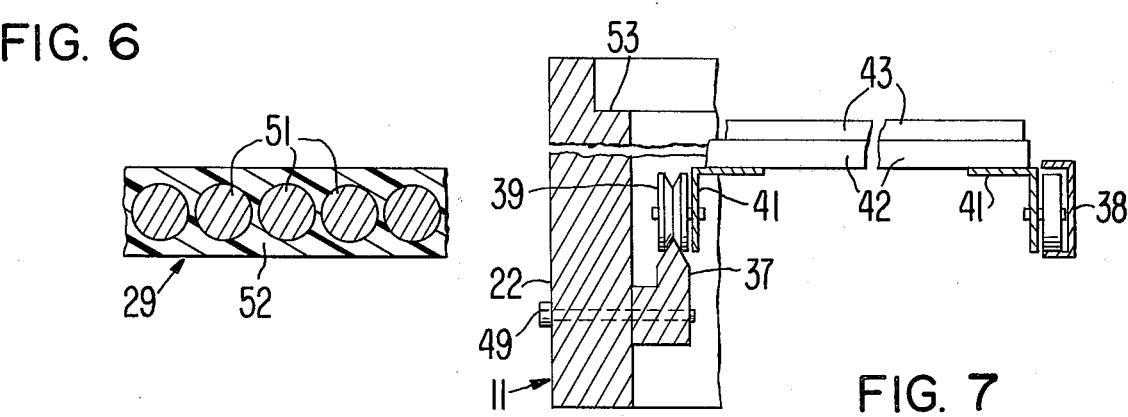
FIG. 6
FIG. 7
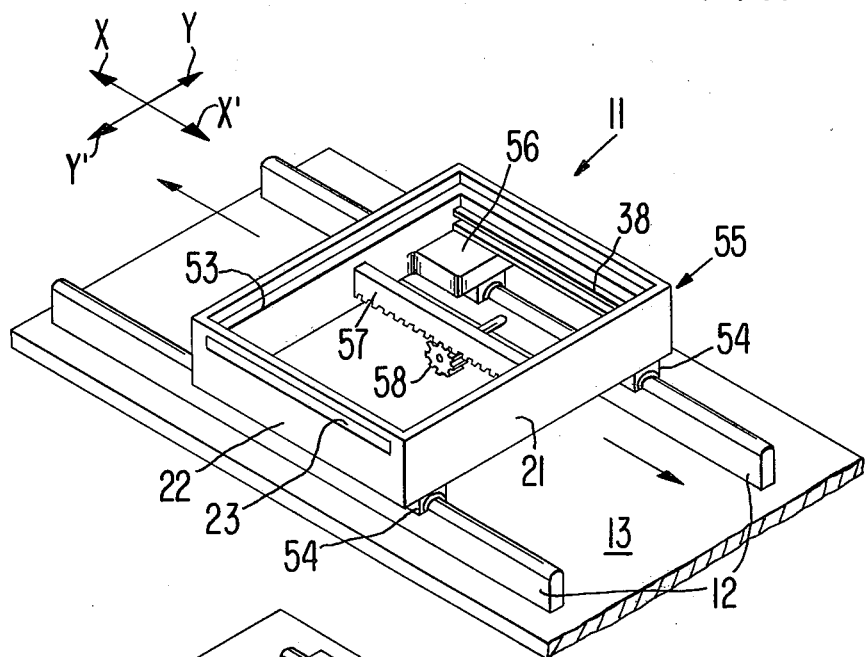
FIG. 8
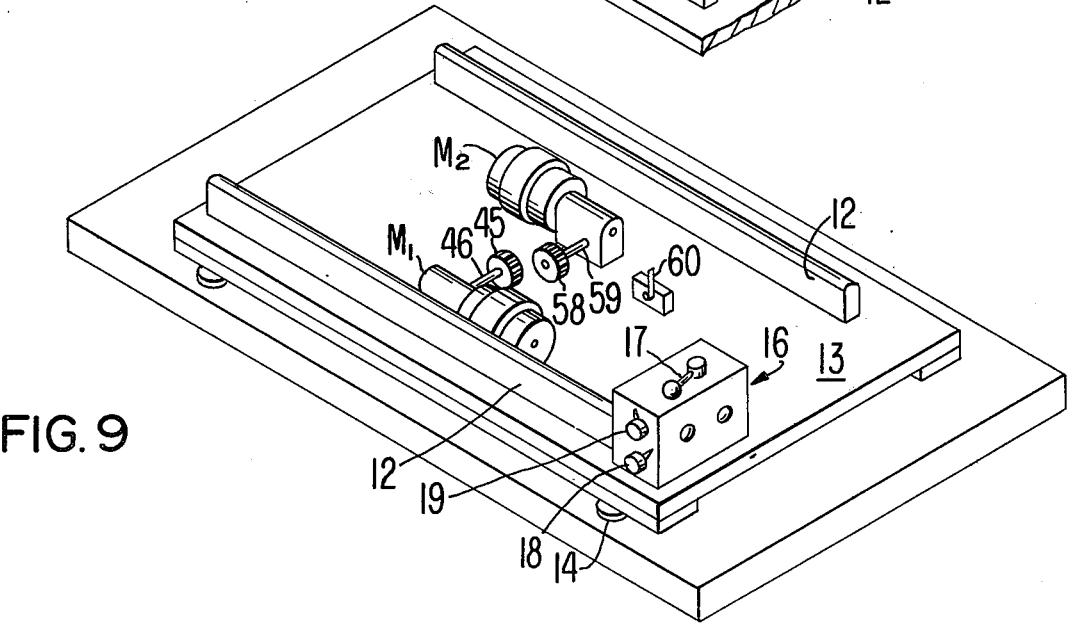
FIG. 9

THREE-DIMENSIONAL RADIOGRAPHY

This invention relates to improvements in X-ray diagnostic techniques and, more particularly, to apparatus and methods for exposing a photographic film to X-rays in a manner to permit images on the exposed film to be viewed in three-dimension by means of a lenticular screen. The conventional X-ray photograph merely shows a two-dimensional view of an object, such as a particular view of the human body. Such a two-dimensional view does not, in many cases, give a diagnostician adequate information as to the extent of a particular disorder, such as the depth of the foreign object in a body part or the displacement of a body part from its normal position.

To overcome some of the limitations of standard two-dimensional X-ray procedures, the concept of tomography was developed. Tomography is a technique of body section radiography in which both the source of X-rays and the film holder are in motion during a particular exposure. However, the X-ray source and film holder move in opposite directions and the holder is on the opposite side of the object to be X-rayed from the source. The effect of tomography is to blur all images on either side of a particular flat plane so that objects in such plane, the focus of rotation, can be isolated from objects out of such plane. While the tomograph, i.e. the film resulting from the practice of tomography represents an improvement over the conventional two-dimensional X-ray photograph, it is also limited as a diagnostic tool for several reasons. For instance, for optimal resolution, the desired X-ray tube motion should be such that it blurs all unwanted shadows. This can be achieved by a wide tube excursion and projection of the X-ray beam through all angles of inclination during the exposure.

Although proper tube movement is essential, other factors also present problems in containing good image resolution. These include the fact that the X-ray equipment must be sufficiently rigid so as to be essentially free of vibration to prevent movement of the film holder during the exposure. Also, proper exposure factors must be properly selected and a high frequency rotating anode for the X-ray tube must be provided with a fractional focal spot. Furthermore, extremely high speed film is required to obtain the proper exposure. Finally, it is imperative that the object to be X-rayed, such as a patient, be completely immobilized during the exposure to assure that the focal point of the X-rays during transit of the X-ray source remain in a single plane.

Because of the foregoing, tomography has been found to be of limited use as a diagnostic tool, giving rise to inaccuracies which often render diagnoses questionable. For instance, a diagnostician cannot, in many cases, determine with accuracy the location and depth of a particular skeletal disorder when utilizing tomography inasmuch as the focal plane of the various X-ray beams may very slightly bring the entire exposure due to one reason or another, such as movement of the patient or vibration of the film holder relative to the patient. The present invention is directed to an improvement in the use of photographs as diagnostic tools and is directed to apparatus and a method for obtaining a photograph of an object using an electro-magnetic radiation source, such as an X-ray tube, isotope, or the like, in a manner to permit the film, when viewed through a lenticular screen, to reveal objects in three-dimension. Thus, not only can the film be viewed for specific size information but it can also be used for determining the specific depths in which certain objects are located relative to a predetermined reference so as to provide diagnostic information which has heretofore been unobtainable from any of the earlier X-ray photographic techniques. The film can also be viewed to measure movements within the object not only laterally, i.e. parallel to the film, but in other planes as well.

The invention has been described herein in connection with X-rays, however, this is for purposes of illustration only since the invention relates to all forms of electro-magnetic radiation which are capable of penetrating a three-dimensional object and recording an image of the interior parts of the object on a recording medium sensitive to the radiation used. Thus, any such radiation is suitable if it provides photographs which permit three-dimensional viewing as hereinafter described.

An essential element in the practice of the present invention is a parallax grating formed of a plurality of generally parallel rods opaque to the radiation used. The rods are spaced apart sufficiently providing grating slits which permit beams of the radiation to pass between the rods and impinge upon the photographic film behind the grating to form a plurality of variable aspect picture elements which are disposed in side-by-side relationship to each other and define linear slit images, there being one slit image behind each grating slit. The panoramic series of aspect views are laterally displaced in neat linear picture elements behind the rods and separately placed upon the film emulsion in the form of a plurality of juxtaposed picture elements. The image formed on the film is sometimes herein referred to as a "parallax panoramagram". After the exposed film has been properly developed, forming an X-ray photograph or radiograph of the parallax panoramagram, it can be used with a lenticular screen for viewing and the lenticular screen can be designed to project the spatial image into an angular field of observer space of a predetermined angle. Thus, upon viewing the picture through the lenticular screen, each eye of an observer sees its own respective aspect view and the observer will, therefore, see a particular stereo pair of picture elements so as to perceive an orthoscopic three-dimensional spatial image of the X-rayed object from any viewing position within the angular field of view.

A more detailed discussion of the parallax grating construction, its operation, and the methods and apparatus for three-dimensional viewing of the developed film are set forth in my co-pending U.S. application Ser. No. 273,653 entitled THREE-DIMENSIONAL RADIOGRAPHY filed July 20, 1972 now abandoned in favor of U.S. application Ser. No. 447,108, filed Feb. 28, 1974, the latter application now abandoned in favor of U.S. application Ser. No. 538,425, filed Jan. 3, 1975, and relevant portions are expressly incorporated herein by this reference.

The present invention is distinguishable from that disclosed in the co-pending application in several respects including that, in the earlier application, a continuum of point sources of X-rays is employed, the continuum extending in a direction perpendicular to the grating rods to provide necessary object exposure from different aspects. Special X-ray generation apparatus was required. The present invention permits the accomplishment of the objects and advantages of the foregoing without a special radiation source.

The primary object of this invention is to provide apparatus and a method for providing a photograph exposed to electro-magnetic radiations in a manner such that the photograph, when viewed through a lenticular screen, permits objects to be viewed in three-dimension.

Another object of this invention is to provide apparatus and method of the type described wherein a photographic film is exposed to radiation beams from a conventional X-ray source while the object and film move laterally relative to the source, the film and object moving in the same direction in parallel planes at different speeds such that the object and film are maintained in congruent alignment with the beam source, while the parallax grating, being fixably mounted to the film support, moves slightly out of congruency so that the beams passing through the grating onto the film undergo slight scanning movements relative to the film as the film and object are traversed whereby aspect views of the objects are recorded on the film in a manner to achieve a three-dimensional effect when viewed with a lenticular screen.

Other objects of this invention will become apparent when the following specification progresses, reference being had to the accompanying drawings for an illustration of the invention.

FIG. 6 is an elevated segment in cross-section of the parallax grating shown in FIG. 5 and taken along the lines 6—6;

FIG. 7 is an elevated section, with parts broken away and foreshortened, of the film tray carriage mounting to the scan table, taken along the lines 7—7 of FIG. 5;

FIG. 8 is a perspective view of the scan table frame mounted for reciprocating travel on parallel rails according to the present invention;

FIG. 9 is a perspective view of the base for carrying the reciprocating scan table as shown in FIG. 8, together with an illustration of the drive motor placement, limit switch mechanism, and control box;

Figure 1:
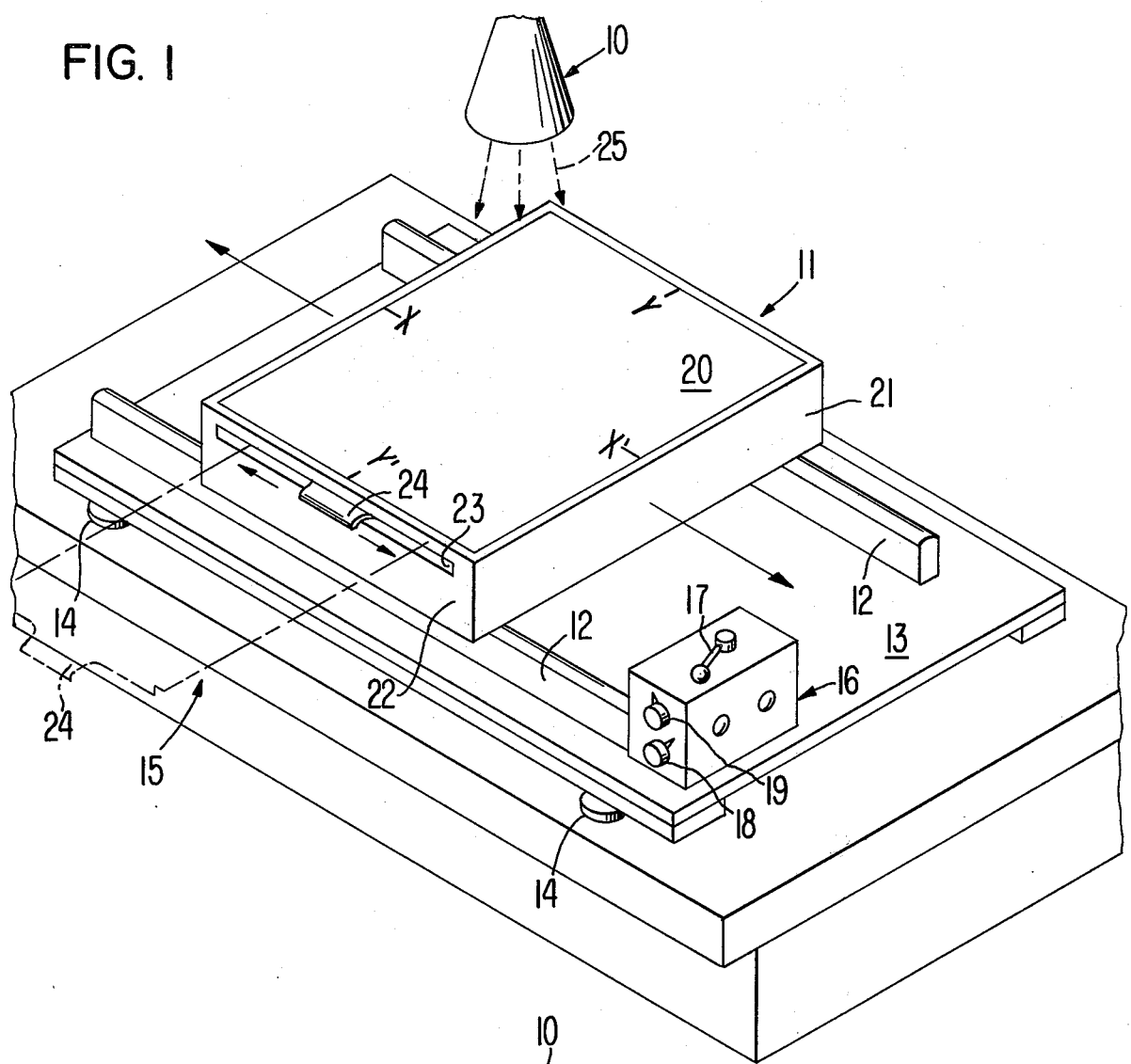
FIG. 1 is a perspective view of the apparatus for obtaining an X-ray photograph which can be used to view images in three-dimension, illustrating the travel directions of the scan table and film tray, as well as showing how the film tray may be withdrawn from the scan table to load and unload film.

The camera or photographic apparatus of the present invention is illustrated in FIG. 1. In FIG. 1, an X-ray source 10 directs a beam of X-rays 25 onto the object support surface 20 (upon which the object to be X-rayed is placed) of the scan table 11. Beneath the object support platform 20, the scan table houses a film tray 15, which may be withdrawn endwise for loading and unloading film as illustrated by dotted lines. The scan table is translatable back and forth in a direction parallel to the X-axis, as indicated, and the film tray is translatable within the housing in the same direction on a carriage (shown in FIGS. 5 and 7.) The scan table has opposed side walls 21 and opposed front and rear end walls 22. The front end wall 22 is provided with a slot 23 through which the film tray handle 24 protrudes. The scan table 11 is mounted for slideable translation in a direction parallel to the X-axis on parallel rails 12 supported by base 13. Base 13 is provided with four levelling screws 14. Control box 16 mounted on the base 13 is provided with a forward/reverse switch 17 which governs the direction of travel of both the scan table and the film tray carriage. Control box 16 also includes dials 19 and 18 which are used to set the translational speed of the film tray and scan table respectively.

Figure 2:
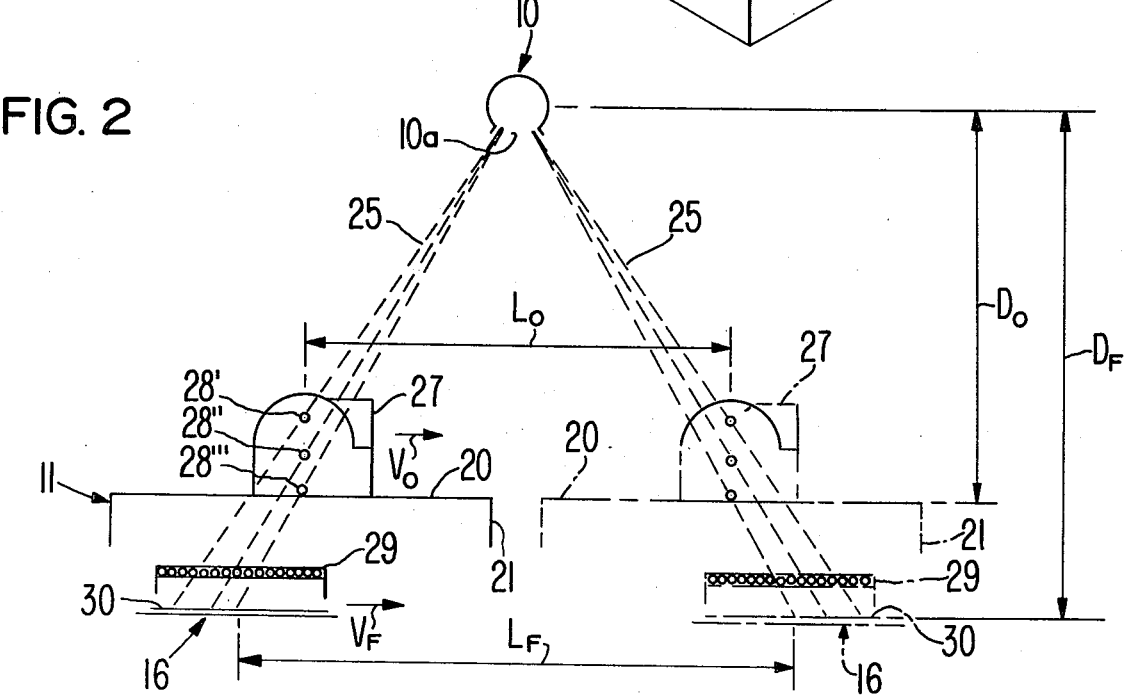
FIG. 2 is a schematic elevation of the system shown in FIG. 1, shown in operational relationship with an object to be photographed.
Figure 5:
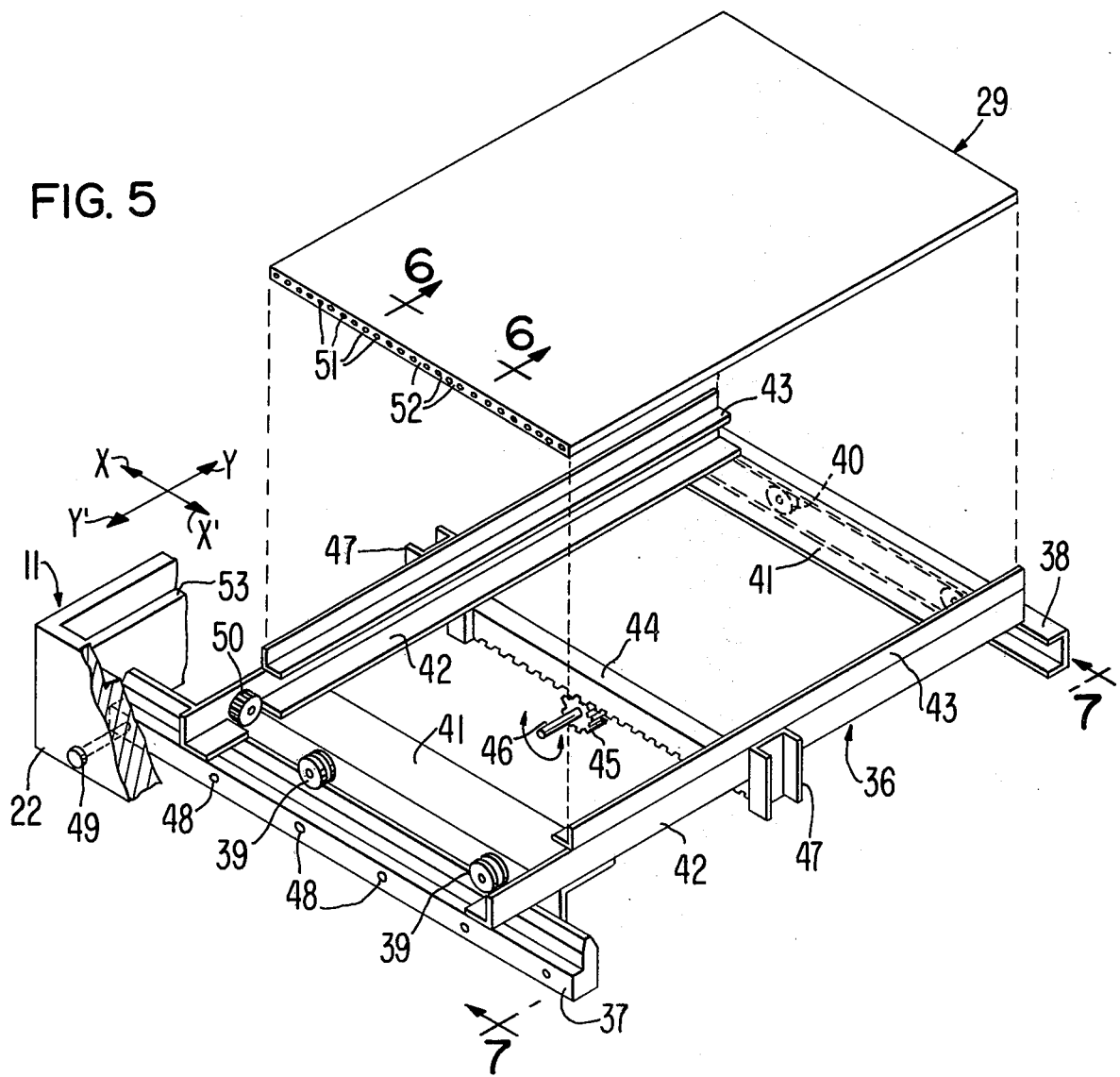
FIG. 5 is a perspective view of the film tray carriage of the present invention, illustrating both its relationship with the parallax grating and its mounting to the scan table 11, shown broken away.

FIG. 2 illustrates operation of the camera shown in FIG. 1. In FIG. 2 a three-dimensional object 27 is supported on the object support platform 20 of the scan table 11. The film tray 15 is shown beneath the scan table 11, supporting film 30. Parallax grating 29 is disposed between the film and the scan table. Object 27, parallax grating 29 and film 30 are all aligned with the X-ray tube 10 so that the X-ray beam 25 emanating from the X-ray tube window 10a passes successively through the object 27, the parallax grating 29, and strikes the film 30. Parallax grating 29 is illustrated and described in detail in connection with FIG. 6 and its mounting relative to the film tray is illustrated in FIG. 5. Briefly, the grating consists of a plurality of transversely circular rods disposed parallel to one another in a plane and closely spaced. The grating rods extend in a direction perpendicular to the direction of travel of the scan table and film tray. The grating rods are opaque to the beam 25 so that only X-rays which pass through the object and strike the film are those which pass between the rods of the grating 29. With the beam activated, the tray 15 and scan table 20 are translated simultaneously in parallel paths transverse to the beam path. Scan table speed $V_o$ and film tray speed $V_f$ are selected to maintain the object support surface 20 of the scan table 11 and the radiation sensitive surface of the film 30 in substantially congruent alignment at all times during their traverse of the exposure field, indicated by $L_o$ and $L_f$ respectively. During traverse, the beams strike the object at a continuum of different angles and an image of each such angle is recorded on the film 30 in a different location for each different aspect view of the object view 27 as "seen" by the beam 25 during traverse. Since only a very small portion of the beam passes through the grating, the image appearing on the film at any given time appears as a plurality of parallel slit images, each of which is relatively widely spaced from the other, and each of which corresponds to a single aspect view of the object 27. During translation, that portion of the beam passing between two parallel rods to form a slit image corresponding to a single aspect view scans along the film surface as the aspect changes, thereby providing a variable aspect picture element beneath each grating space or slit at the end of the traverse. The viewing field arc, grating dimensions, and grating-to-film spacing are all selected so that the end of the traverse $L_f$, the film has been imaged with a plurality of variable aspect picture elements disposed in side-by-side relationship to each other, there being one such picture element for each slit in the grating.

It will be appreciated that, since the position of the grating 29 is fixed relative to the film 30, as the scan table 11 and film tray 15 traverse the viewing field, selection of scan table and film tray velocities to maintain the support surfaces of those members in congruent alignment with the X-ray source 10 will maintain the grating 29 in alignment therewith but not in "congruent alignment" as that term is intended to be understood herein, during traverse. In one sense, it is the absence of congruency of the grating relative to the other elements during traverse together with the existence of congruency of the scan table and film tray which results in the unique operation of the camera of the present invention. Desired alignment during traverse will be accomplished if the means for supporting the object and film are translated at rates $V_o$ and $V_f$ respectively, where $V_f \cdot V_o = D_f \cdot D_o$, if $D_f$ and $D_o$ are the respective distances of the film and object supporting means from the X-ray tube.

The film tray 15 and object support surface 20 of the scan table move in planes established at predetermined fixed distances $D_f$ and $D_o$, respectively, from the X-ray tube 10. Different internal features of the object 27, located at vertically spaced position, are illustrated at 28', 28" and 28'''. The X-ray tube 10 may be selected from any one of a number of suitable conventional X-ray tubes. The tube window 10a should be sufficiently wide to provide a beam which will encompass the entire target area of the object 27 in both the x and y directions during traverse. If the X-ray tube window 10a is not great enough to cover the target area in the x direction during traverse, the tube may be pivoted during traverse movement, if necessary.

Figure 3:
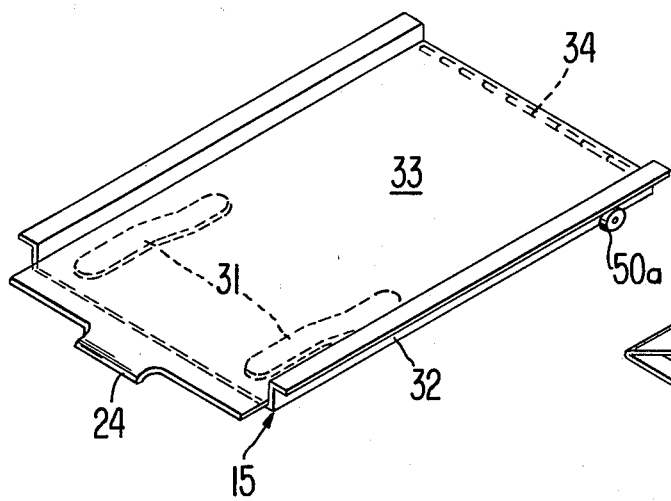
FIG. 3, is a perspective view of the film tray of the present invention.
Figure 4:
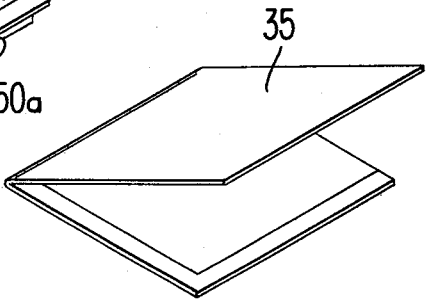
FIG. 4 is a perspective view of a film cassette for loading in the film tray of the present invention.

FIG. 3 illustrates a film tray 15 suitable for use in the present invention and which is comprised of a base 32 and lid 33 fastened together at their rear edges with a hinge 34, whereby the lid 33 may be lifted for loading and unloading of a conventional X-ray film cassette 35, as illustrated in FIG. 4. Leaf springs 31 mounted on the tray base 32 urge the lid 33 upwardly, so that when the film tray is inserted into the film tray carriage 36, the lid urges against the bottom of the grating side supports 43 to hold the tray securely in position. The tray handle 24 is depressed to withdraw the tray 14 from the carriage 36.

FIGS. 5 and 7 illustrate the construction details of the film tray carriage 36. The carriage 36 is comprised of two parallel angle beam film tray side supports 42 attached to parallel angle beam film tray end supports 41 forming a rectangular frame. Angle beam grating side supports 43 are mounted on the upper edges of tray side supports 42 and support parallax grating 29 at its two lateral edges. The carriage 36 is supported at one end with rollers 39 mounted on the end support 41. Rollers 39 rise on mounting rail 37 attached to the inner vertical surface of end wall 22 of the scan table 11 by means of bolts 49 extending through apertures 48 in the mounting rail 37. Film tray carriage 36 is supported at its other end by rollers 40 mounted on the rear end wall 41 which track in roller channel 38 formed in the rear end wall 22 of the scan table 11. The horizontally extending portions of carriage side supports 42 and grating side supports 43 form a channel to receive the film tray 15 endwise in the manner illustrated by FIG. 1. Rollers 50 and 50a mounted on the side support 42 and tray 15, respectively, facilitate insertion and removal of the film tray. A gear rack 44 is mounted with brace 47 to span the underside of the carriage frame 36 between side supports 42. Pinion gear 45 mounted on drive shaft 46 extending from motor M1 (shown in FIG. 9, but not in this view) meshes with rack 44 to drive the carriage 36 back and forth along the X-axis of the system. It will be appreciated that this arrangement permits the film tray carriage 36 to be driven independently of the scan table 11 even though it is supported by the scan table.

As shown in FIG. 6, the parallax grating 29 is comprised of a plurality of spaced, parallel, transversely circular rods 51 which are made of a material opaque to X-rays, such as lead or tungsten. These rods are fixed relative to each other such as by being embedded in a rigid matrix panel 52 of a suitably molded material, such as thermoplastic resin or the like. The matrix panel 52 may be formed of formica, bakelite or other suitable material.

Each rod 51 can be of any desired diameter to achieve the aspect views of object 27 on the film 30, since different systems constructed with different geometry enable different gratings to be employed. Nevertheless, the rods 51 are preferably 0.020 inches in diameter and slit spacing between the rods is preferably 0.002 inches. It is preferred to have the ratio of rod diameter to rod spacing on the order of approximately 10:1. As illustrated in FIG. 5, the rods 51 in the grating 29 are disposed parallel to the Y-axis.

FIG. 8 illustrates how the scan table frame 55 is mounted on parallel rails 12 for reciprocating translation in a direction parallel to the X-axis. Frame 55 is supported at its four corners on four half-sleeve ball races 54 and preferably is a unitary aluminum casting. Frame 55 is comprised of side walls 21 and end walls 22 which form an open rectangular frame with an offset ledge 53 at the upper edges of the walls 21 and 22 for supporting the object platform 20, preferably a magnesium plate (as shown in FIG. 1, but not in this view). Corner abutments 56 provide mountings for the ball races 54. Roller channel 38 for mounting the rear end of the film tray carriage 56 is integrally formed on the inner vertical surface of the rear end wall 22 of the frame 55. A gear rack 57 spans the underside of the frame 55 between the side walls 21. Pinion gear 58 attached by drive shaft 59 to motor M2 (shown in FIG. 9) drives the scan table along the X-axis. The positions of the scan table and film carriage drive motors M2 and M1, respectively, are shown in FIG. 9, together with the position of a limit switch 60 useful in halting the traverse of the scan table 11. Control box 16 includes forward/reverse lever 16 which drives both motors M1 and M2, together with dials 18 and 19 for setting the speeds of motors M2 and M1, respectively.

Figure 10:
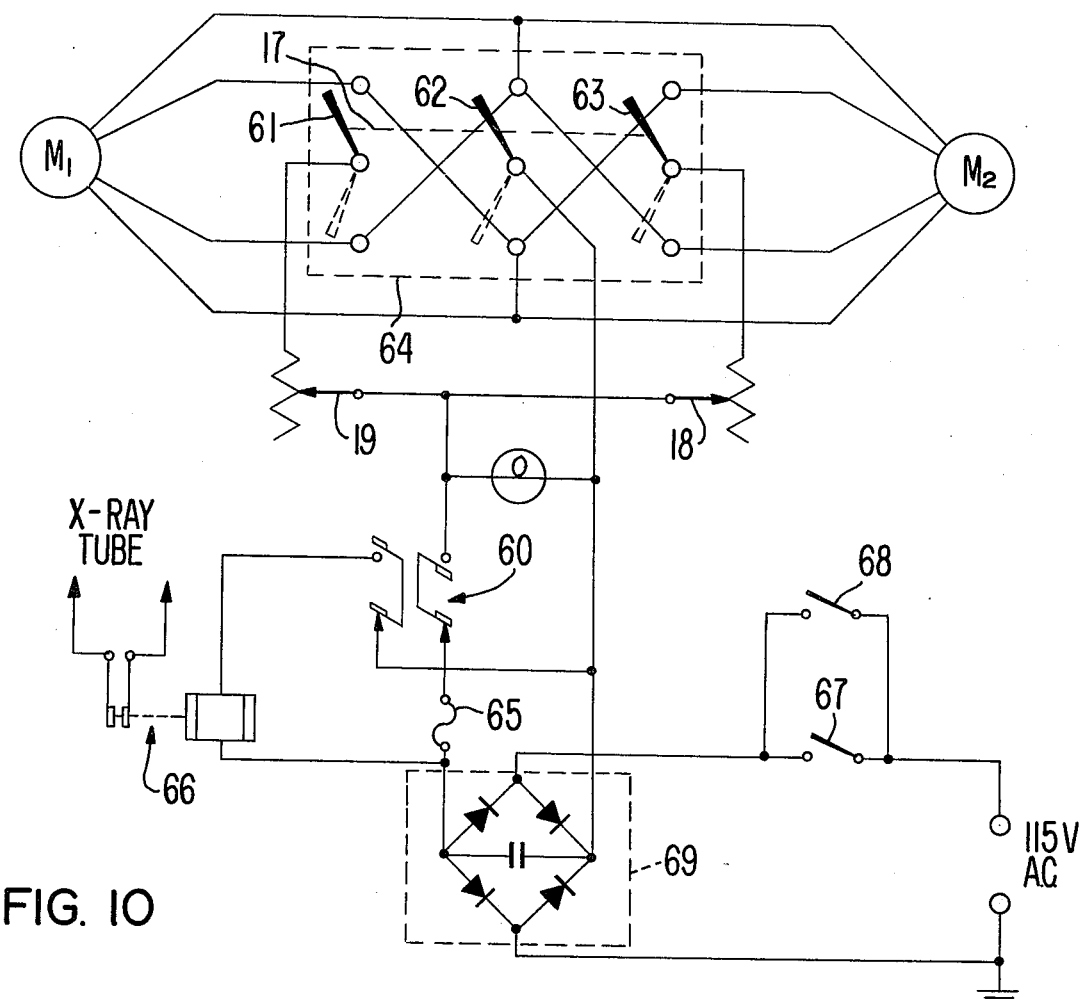
FIG. 10 is a diagram of the electrical circuit utilized in providing power and controls for the camera apparatus illustrated in FIGS. 1–9.

FIG. 10 illustrates a suitable electrical circuit for the system disclosed in FIGS. 1 through 9. Main power switch 67 and remote power switch 68 are employed to switch power on and off from a 115v alternating current power source which is converted to direct current by a four-diode rectifier 69. When the power is turned on, relay switch 66 activates the X-ray tube and power is supplied, via variable resistances 18 and 19, to motors M2 and M1, respectively. Direction of the motors M1 and M2 is controlled by 3 PDT switch 64. Switch 64 includes contactors 61, 62 and 63 which are ganged for simultaneous action in response to forward and reverse lever 17. Limit switch 60 controls both the motors and X-ray tube.

To take a radiograph, i.e. to subject the film to radiographic exposure, utilizing the apparatus disclosed and described in connection with FIGS. 1 to 10, herein, a film cassette 35 is first loaded into the film tray 15 which is inserted endwise through the slit 23 into the scan table housing 11. The object (or objects) to be X-rayed is placed on the object support surface 20 and the X-ray tube 10 is set at a convenient distance (D) above the center of the object support surface of the support platform 20. Previously, the film tray carriage 36 and scan table 11 have been set at the left (x) end of the traverse. Main power switch 67 is closed to activate the X-ray tube and to drive the scan table and film tray to traverse distances $L_o$ and $L_f$, respectively, permitting the X-ray tube 10 to project a continuum of aspect views of the internal structures of the object 27 upon the film 30. Total exposure may be from 1 second up to several minutes if desired. The successive aspect views of the object planes are projected through the grating 29 positioned a predetermined distance above the radiation sensitive surface of the film 30. Upon completion of the traverse, the film tray 15 is withdrawn and the film cassette removed so that the film may be unloaded for processing.

It will be appreciated that the scan table and film carriage may be traversed in either direction along the X-axis so long as they are traversed in the same direction at the same time to maintain congruent alignment as previously described.

Figure 11:
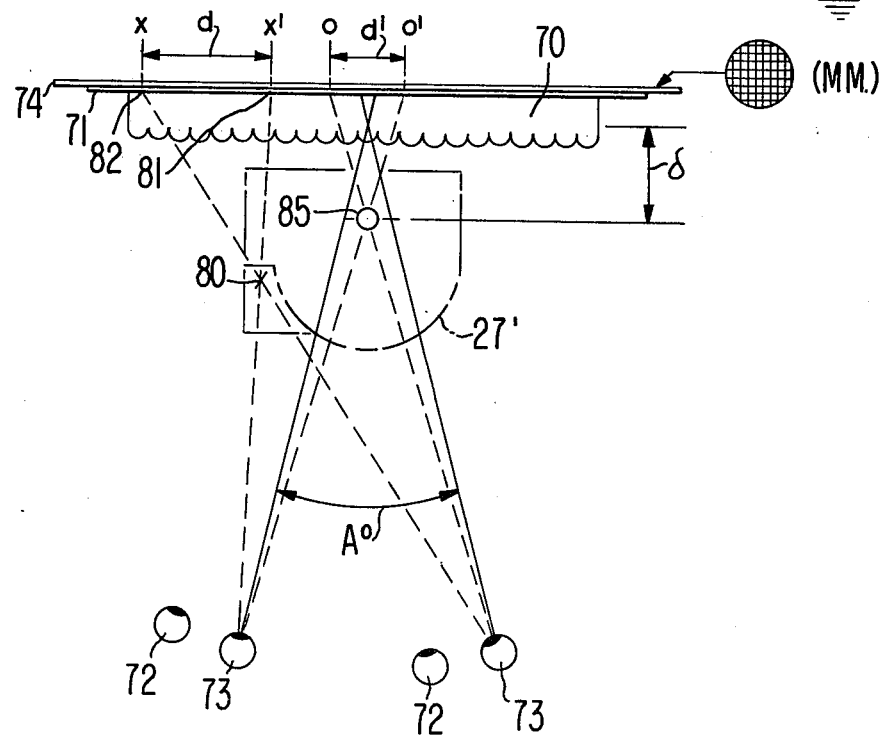
FIG. 11 is a top plan view illustrating how a lenticular screen is utilized for three-dimensional viewing of films exposed and developed in accordance with the principles of the present invention.

The developed film is viewed with apparatus shown in FIG. 11. In this apparatus, a lenticular screen 70 is placed in registry with the juxataposed variable aspect picture elements and held flat against the film surface for viewing. The film, in turn, is held firmly against the flat window 74 of an illuminator. The lenticular screen 70 is designed to project the spatial image on the film into an angular field of observer space of an arc angle A°.

Upon viewing the picture through the screen 70, each eye of an observer represented by left and right eyes 72 and 73 respectively, sees its own respective aspect view. Because the eyes are separated by a normal pupillary distance of about 2 ⅜ inches, the observer will see a stereo pair of images and will perceive an orthoscopic three-dimensional image of the object 27' or some particular part thereof from any viewing position within the angular field of view. Depth planes of the spatial images commence at zero depth at the optical center of the lenticular screen and increase in even increments in the observer space to the nearest plane visible in the spatial image.

Lenticular screen 70 must be constructed to match the number of grating lines per inch of the grating 29 through which the X-ray beams pass. The angular aperture A° of each lens ridge of the screen 70 is greater when the screen is thin and narrower when the screen is thick. a preferred angular aperture A° is 23°. This will allow the viewer to move laterally in a field about 3 times wider than his pupillary separation when he is viewing from the closest or minimum view point. He will see the spatial image in orthoscopic perspective when viewing from any desired viewing position within this angular observer space. FIG. 11 illustrates how "depth" measurements can be made utilizing the developed film 71. For instance, when the film is viewed through the screen 70 and the viewer moves across the viewing field A°, from one side to the other, the image of a subject point is seen to move laterally across the film. When one eye, (for example right eye 73,) of the viewer is located at the left hand side of the viewing field, the viewer will see object 80 imaged at position 81. When the eye 73 is in the right hand position of FIG. 11 the observer will see object 80 imaged at position 82. Positions 81 and 82 are separated by a displacement d and, regardless of the direction of movement of the eye from left to right or right to left, displacement d will always be the same.

When a grid line is pre-exposed on the film or is simply held against the film surface, the viewer can read the displacement d in the units of the grid line, for example, in millimeters as shown in FIG. 11. When the target to cross over plane of grating distance [D], the scan length [$L_o$], and the disparity [d] (in millimeters) for instance, are known, then the depth [$\delta$] position of the subject point is given by the equation:

$$\delta = \frac{(D-\delta)d}{L_o}$$

When D and L are held constant, the displacement readings can be plotted against depth increments on a curve so that reference to such a curve readily provides depth measurements for empirically determined displacement values. FIG. 11 also shows that another object 85 having a greater depth than the object 80 will have displacement d' less than that of the object 80. Thus, due to perspective, the shadow of an internal feature increases in width directly with its depth position in the x-rayed object so that the actual or "real" width $W_r$ of a structure can be determined after its depth $\delta$ is known by the equation:

$$W_r = \frac{D \cdot W_o}{D - \delta}$$

where $W_o$ is the measured shadow width of the structure as determined, for example, on the millimeter grid. The apparatus can be calibrated for different D settings to develop magnification factors (m) for objects where $W_o$ and $\delta$ are known so that the real width $W_r$ of an internal structure can be determined by the equation:

$$W_r = m \cdot W_o$$

The apparatus of the present invention is also suitable for measuring the distance moved by an internal feature in the object X-rayed. For example, the path traced by the object can be measured against the coordinate grid in millimeters and, if the movement is only lateral, the exact distance of the movement is determined in the same manner as in determining real width of a stationary object. Movements outside of the lateral plane can also be measured when the direction of movement within the object is known, together with the depth $\delta$ of both the initial and final positions of the object.

The invention has been described with particular reference to a certain preferred embodiment thereof, and it will be understood that variations and modifications can be effected within its spirit and scope.

I claim:

1. Apparatus for obtaining a radiograph of a three-dimensional object comprising:
   a source of electro-magnetic radiation capable of penetrating the object;
   first support means for supporting a recording medium sensitive to the radiation in the path of radiation from said source;
   a parallax grating mounted on said first support means between the recording medium and said source;
   second support means for supporting the object between said source and said first support means; and
   means for translating said first and second support means simultaneously in parallel paths transverse to the beam path at different rates of speed to maintain the first and second support means in congruent alignment with the beam source during said translation.

2. Apparatus as recited in claim 1 wherein said parallax grating includes a plurality of parallel, spaced, transversely circular rods opaque to said radiation disposed in a plane spaced a predetermined distance from the position of the recording medium surface, said rods oriented perpendicular to the direction of translation of said first and second support beams.

3. Apparatus as recited in claim 1 wherein said source is an X-ray tube.

4. Apparatus as recited in claim 1 wherein said second support means includes a platform slideably mounted on a base, and at least one wall extending downwardly from the platform, and wherein said first support means includes tray suspended from said wall for slideable movement beneath the object bearing surface of said platform.

5. Apparatus as recited in claim 4 wherein said end wall is provided with a slot through which said tray may be removed from beneath said platform to facilitate loading and unloading of radiographic film constituting the recording medium.

6. Apparatus for obtaining a radiograph of a three-dimensional object comprising:
   means for producing a beam of electro-magnetic radiation capable pf penetrating the object;
   means for supporting the object to be radiographed in the beam path at a distance $D_o$ from said beam producing means;
   means for supporting a record medium sensitive to the radiation in the beam path in alignment with said object support means and said beam producing means, said record medium support means located at a distance $D_f$ from said beam producing means, where $D_f$ is greater than $D_o$;
   a grating mounted on said record medium support means a predetermined distance from the position of the radiation sensitive surface of the record medium between said position and said object support means; and
   means for simultaneously translating said object support means and said record medium support means in the same direction laterally relative to the beam source at rates $V_o$ and $V_f$, respectively, where $V_f : V_o = D_f : D_o$.

7. Apparatus for obtaining a radiograph of a three-dimensional object comprising:
   means for producing a beam of electro-magnetic radiation capable of penetrating the object;
   means for supporting the object to be radiographed in the beam path at a distance $D_o$ from said beam producing means;
   means for supporting a record medium sensitive to the radiation in the beam path in alignment with said object support means and said beam producing means, said record medium support means located at a distance $D_f$ from said beam producing means, where $D_f$ is greater than $D_o$;
   a grating mounted on said record medium support means a predetermined distance from the position of the radiation sensitive surface of the record medium between said position and said object support means, said grating being comprised of a plurality of transversely circular rods opaque to the radiation, said rods extending in a direction perpendicular to the translational direction of said object support means and said recording medium support; and
   means for simultaneously translating said object support means and said record medium support means laterally relative to the beam source at rate $V_o$ and $V_f$, respectively, where $V_f : V_o = D_f : D_o$.

8. Apparatus as recited in claim 7, wherein each of said rods have a diameter approximately 10 times as great as the spacing between the rods.

9. Apparatus as recited in claim 7, wherein each of said rods is approximately 0.020 inches in diameter and wherein the spaces between the rods are approximately 0.002 inch wide.

10. A method of obtaining a radiograph of a three-dimensional object comprising:
    providing a beam of electro-magnetic radiation capable of penetrating the object and a recording medium sensitive to that radiation;
    placing the object between the beam source and the medium;
    simultaneously translating the object and recording medium relative to the beam source in parallel paths transverse to the beam path to maintain the beam source, object, and recording medium in congruent alignment; and
    translating a parallax grating transverse to the beam source in a direction parallel to the paths of the object and recording medium at a rate sufficient to maintain the grating in alignment, but not congruent alignment, with the object and recording medium, whereby those portions of the beam passing through the grating scan the recording medium to form a plurality of images of portions of the object viewed from different directions.

11. A method of obtaining a radiograph of a three-dimensional object comprising:
    providing a beam of electro-magnetic radiation capable or penetrating the object;
    directing the beam through the object onto a radiographic recording medium;
    blocking the beam at spaced, elongate, parallel, coplanar, transversely circular regions before the beam reaches the recording medium whereby only those portions of the beam passing between the blocking regions will reach the radiographic recording medium; and
    translating the object, recording medium and blocking regions simultaneously in the same direction laterally relative to the beam path to maintain the object and recording medium but not the regions in congruent alignment in the beam path.

12. Apparatus for obtaining a radiograph of an object comprising:
   base;
   a source of electro-magnetic radiation positioned a predetermined distance above said base;
   a scan table mounted on said base beneath said source of radiation for movement in a direction parallel to said base, said scan table having an upper surface for supporting the object to be radiographed;
   a carriage for supporting a record medium sensitive to the radiation, said carriage mounted beneath said scan table for movement parallel to said base and in the same direction as said scan table;
   a grating including a plurality of parallel, spaced, transversely circular rods, each rod being opaque to the radiation, said grating mounted on said recording medium carriage between the position of the recording medium and the object support surface of the scan table; and
   means for driving said scan table and said carriage simultaneously at different rates of speed to maintain the object support surface of said scan table and the position of the radiation sensitive surface of the recording medium in congruent alignment with the source of electro-magnetic radiation.

13. Apparatus as recited in claim 12 wherein the recording medium is radiation sensitive film and further comprising a film tray supportable on said carriage beneath said grating, said tray slideable endwise from beneath said grating for loading and unloading the film.

14. Apparatus as recited in claim 12 wherein said carriage is mounted to said scan table beneath the object support surface and is movable in a direction parallel and relative to the object support surface on said scan table.

15. Apparatus as recited in claim 12 wherein said scan table includes a wall extending downwardly from the object support surface and wherein said carriage is mounted on said wall beneath said object support surface for movement parallel therewith.

16. The apparatus of claim 12 wherein there is further provided a tray for carrying the record medium which is slideable endwise into said carriage beneath said grating for loading and unloading the recording medium from the apparatus.

* * * * *